United States Patent
Roggeman et al.

(10) Patent No.: US 6,723,888 B2
(45) Date of Patent: Apr. 20, 2004

(54) HUMIDIFICATION OF HYDROCARBON MIXTURES FOR USE IN POLYMER SYNTHESIS

(75) Inventors: David M. Roggeman, North Royalton, OH (US); James Oziomek, Cuyahoga Falls, OH (US); Timothy L. Tartamella, Silver Lake, OH (US)

(73) Assignee: Bridgestone Corporation, Tokyo (JP)

( * ) Notice: Subject to any disclaimer, the term of this patent is extended or adjusted under 35 U.S.C. 154(b) by 241 days.

(21) Appl. No.: 09/808,508

(22) Filed: Mar. 14, 2001

(65) Prior Publication Data

US 2002/0132942 A1 Sep. 19, 2002

(51) Int. Cl.$^7$ .............................. C10M 105/02
(52) U.S. Cl. .......................................... 585/3
(58) Field of Search .................................. 585/3

(56) References Cited

U.S. PATENT DOCUMENTS

| | | | |
|---|---|---|---|
| 3,778,424 A | 12/1973 | Sugiura et al. | 260/94.3 |
| 4,182,813 A | 1/1980 | Makino et al. | 526/92 |
| 4,182,814 A | 1/1980 | Bernemann et al. | 526/92 |
| 4,472,559 A | 9/1984 | Maehara et al. | 526/92 |
| 4,705,654 A * | 11/1987 | Niwa et al. | 261/128 |
| 5,109,082 A | 4/1992 | Matsuda et al. | 526/93 |
| 5,346,971 A | 9/1994 | Hongyo et al. | 526/94 |
| 5,548,045 A | 8/1996 | Goto et al. | 526/161 |
| 5,955,553 A | 9/1999 | Oziomek et al. | 526/124.1 |
| 6,096,840 A | 8/2000 | Bernier et al. | 526/68 |
| 6,117,956 A | 9/2000 | Luo | 526/145 |
| 6,514,634 B1 * | 2/2003 | Rush, Jr. | 429/17 |

FOREIGN PATENT DOCUMENTS

| | | |
|---|---|---|
| FR | 2.225.199 | 11/1974 |
| FR | 2.321.318 | 3/1977 |

* cited by examiner

*Primary Examiner*—Thuan D. Dang
(74) *Attorney, Agent, or Firm*—Ann M. Skerry; Meredith E. Palmer

(57) ABSTRACT

A humidification system (A) for humidifying a dry hydrocarbon stream includes a column (10) which defines an interior cavity (20). The cavity is partially filled with a bed (12) of a packing material (40) and a layer of water (20), leaving a headspace above the water. An inlet (52) adjacent a lower end of the cavity receives a dry hydrocarbon stream which is broken up by the packing material and dissolves water as it passes therethrough. Entrained water droplets fall out of the wet blend in a disengagement zone (70) above the water layer leaving the hydrocarbon stream humidified yet substantially free of liquid water in an upper region (72) of the column.

16 Claims, 2 Drawing Sheets

HUMIDIFICATION OF HYDROCARBON MIXTURES FOR USE IN POLYMER SYNTHESIS

FIELD OF THE INVENTION

The present invention relates to humidification of hydrocarbons, such as butadiene, prior to catalytic polymerization, and will be described with particular reference thereto. It should be appreciated, however, that the process is also applicable to other fluids in which water is poorly soluble.

BACKGROUND OF THE INVENTION

The polymerization of 1,3-butadiene to form cis-1,4-polybutadiene with the aid of Ziegler-Natta type catalysts, such as those incorporating aluminum alkyls, alkyl chlorides, or aluminum alkoxides with a transition element, such as cobalt or nickel, is known. The presence of controlled amounts of water in certain transition metal-catalyzed polymerizations, such as the polymerization of butadiene, has been found advantageous for the activation of the catalyst. In particular, small amounts of dissolved water, of the order of 10 to 200 ppm, have been found to be beneficial to the catalytic activity.

Water may be introduced by a dispersion in the reactants themselves, e.g., 1,3-butadiene, or in the solvents such as hexane. In one method, water is passed through a porous frit material into a stream of the hydrocarbon mixture. In other methods, water is introduced to the polymerization reactor. Another method of introducing water employs a cyclone. However, the presence of undissolved water in liquid form in the polymerization reactor has been found to be deleterious to the catalyst, leading to inactivation. Prior methods of incorporating water have often resulted in the presence of water droplets in the hydrocarbon feed.

The present invention provides a new and improved apparatus and method for humidification of a hydrocarbon, which overcomes the above-referenced problems and others.

SUMMARY OF THE INVENTION

According to one exemplary embodiment, the invention provides a method of humidifying a hydrocarbon stream wherein the hydrocarbon stream is passed through a bed including a packing material and water, thereby forming a humidified hydrocarbon stream having water dissolved therein.

According to another exemplary embodiment, an apparatus for humidifying a hydrocarbon stream is provided. The apparatus includes a vessel which defines an interior cavity. A bed of a packing material is disposed in the cavity. Water fills at least a portion of the bed. An inlet adjacent a lower end of the cavity receives a hydrocarbon stream.

The present invention can produce a hydrocarbon stream that is humidified without entraining liquid water.

Additionally, the level of water in the hydrocarbon stream may be controlled.

DESCRIPTION OF THE PREFERRED EMBODIMENTS

Figure 1:
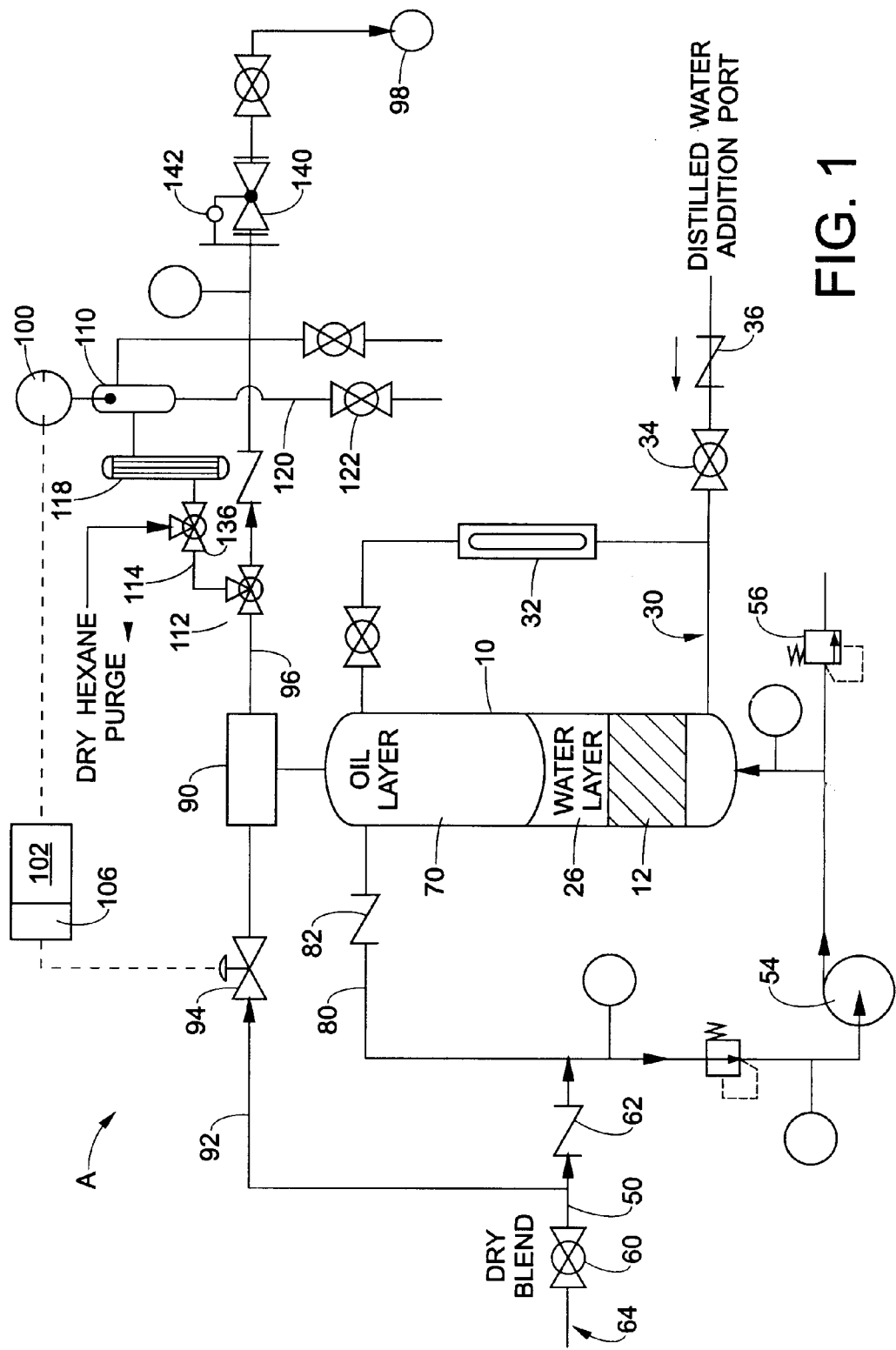
FIG. 1 is a schematic view of a system for humidification of hydrocarbons according to the present invention.

With reference to FIG. 1, a system A for humidifying a hydrocarbon stream is shown. The system dissolves water in the hydrocarbon stream at or below its saturation limit and ensures that little or no free (i.e., undissolved) water exists in the final process stream as water droplets. The hydrocarbon stream can be a single hydrocarbon in liquid or gaseous form or a mixture of hydrocarbons, such as a reactive monomer in an inert solvent.

Exemplary hydrocarbon monomers include monounsaturated alkenes, such as ethene, propene, butene, and conjugated dienes, such as butadiene, isoprene (1,3-butadiene), 2,3-dimethyl-1,3-butadiene, 1,3-pentadiene, 1,3-hexadiene, and the like, and styrene and its derivatives, and combinations thereof. The system is particularly useful for hydrocarbon monomers in which water is poorly soluble, such as butadiene.

Suitable solvents include aliphatic, aromatic, or cycloaliphatic hydrocarbons, examples of which are butane, pentane, hexane, toluene, benzene, cyclohexane, and the like. In one embodiment, the hydrocarbon stream includes a mixture of butadiene and hexane in a ratio of from 1:0 (i.e., pure butadiene) to 1:20.

In an alternative embodiment, one or more components of a hydrocarbon stream is humidified and then mixed with other component(s) of the stream downstream of the column 10. This is particularly preferred when one of the components of the hydrocarbon stream has a lower water saturation level than the others. When relatively high water concentrations are desired, the component having a poor water solubility may be omitted from the hydrocarbon(s) to be humidified and added to the humidified component(s) prior to processing. For example, in the case of butadiene and hexane, butadiene has a saturation level of around 700 ppm at room temperature while hexane has a saturation level of around 200 ppm. The butadiene may be humidified alone to a water content of, for example, above 200 ppm and then the hexane is added to the humidified butadiene prior to processing. Preferably, the butadiene is humidified to a level below that at which water would drop out of the combined butadiene/hexane mixture once the hexane is added.

The hydrocarbon stream leaves the system with dissolved water up to the saturation limit of the hydrocarbon stream. For example, a hexane-butadiene mixture may be saturated up to about 200 ppm water, depending on the composition of the stream.

Figure 2:
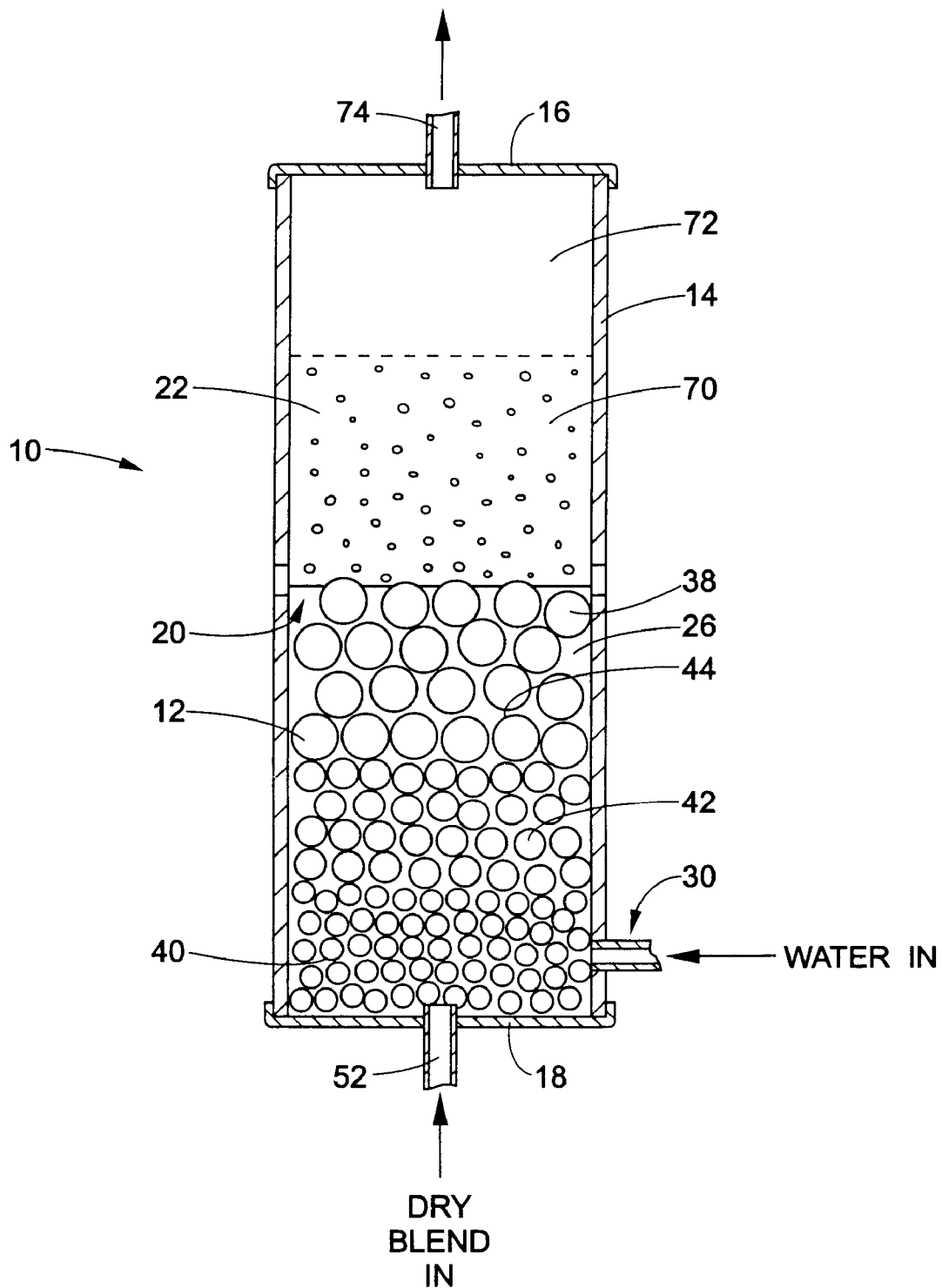
FIG. 2 is a side sectional view of the column of FIG. 1.

With reference also to FIG. 2, the dissolution of water in the hydrocarbon stream may take place in a cylindrical column 10, which is packed with a bed 12 of a dispersion material. The column 10 is formed from a structural material, preferably a non-reactive metal, such as steel, and has a cylindrical side wall 14 closed at upper and lower ends by flanges 16, 18. The dispersion material 12 partly fills an interior 20 of the column, preferably, about the lower half, leaving a head space 22 which is free of the dispersion material.

A water zone 26 fills the column interior approximately up to the top of the dispersion material, i.e., approximately the lower half of the column, and fills the voids in the column packing 12. Preferably, the water covers the packing material, although the water level may drop during humidification process such that the packing material is not fully covered but only partially covered by the water. The water, which is preferably distilled or otherwise purified is introduced to the column through an inlet line 30 adjacent the lower end of the column. A liquid level gauge 32 can be used to adjust the height of the water to the desired level. Once the desired water level is achieved, a valve 34 in the inlet line is closed and the column is ready to receive the hydrocarbon stream. The valve may be a non-return valve, or have a non-return valve 36 associated therewith for inhibiting backflow from the column.

The bed 12 is preferably formed from small beads 38 (not shown to scale) formed of an inert material, such as porcelain. Preferably, the beads are spherical in shape, although other configurations are also contemplated. In a preferred embodiment, the beads range in size from smaller at the bottom to slightly larger at the top of the bed. As shown in FIG. 2, this size configuration can be achieved using a lower layer 40, in which the beads have a diameter of about 0.2–0.4 cm, an intermediate layer 42, in which the beads have a diameter of about 0.5–0.8 cm and upper layer 44, with 1.0–1.5 cm diameter beads. In another embodiment, the particles in the bottom layer have an average diameter of approximately 0.2 to 0.5 centimeters and the particles in the top layer have an average diameter of approximately 1 to 1.5 centimeters. Alternatively, the beads may be of the same size throughout the column. Bead size and arrangement will depend on factors such as the height of the column and the desired flow rate through the bed 12.

In this exemplary embodiment the column is about one meter in height and 10–20 cm in diameter with the beads occupying the lower 40–50 cm. The smaller the beads and the higher the bed, the greater the reduction in flow rate. However, smaller beads tend to break up the hydrocarbon stream into droplets more quickly. Thus, there is a compromise between the size of the beads and the desired flow rate. An exemplary bead size ranges from about 0.2 cm to 1.5 cm expressed in average bead diameter.

The hydrocarbon stream is introduced to the column interior through an inlet line 50 via an inlet port 52 in the lower flange 18. The hydrocarbon stream is preferably introduced as a dry blend. By "dry" it is meant that the hydrocarbon or blend is essentially free of water. However, the blend can contain water, as dissolved water and/or water droplets, because the water droplets, where present, are advantageously removed by the system.

A pump 54, such as a gear pump in the inlet line, pressurizes the dry blend to a pressure of about 10 kg/cm$^2$. Excess pressure may be relieved through a pressure relief valve 56 which is set at just below the maximum pressure desired, e.g., about 13 kg/cm$^2$. A valve 60 in the inlet line 50 may be closed or adjusted to reduce or stop the flow of the hydrocarbon stream into the column. A non-return valve 62 prevents backflow of the stream to its source 64.

The entering hydrocarbon stream passes through the water and packed bed 12. The dispersion material breaks up the stream into numerous narrow pathways and provides a high surface area of contact between the hydrocarbon stream and the water. The hydrocarbon stream is rapidly broken into small droplets that come into contact with the surrounding water, dissolving a portion of the water into each droplet. The hydrocarbon, being lighter than the water, continues upwards into a disengagement zone 70, above the water layer. In the disengagement zone, any undissolved, entrained water falls back down into the bed, due to its higher density. The hydrocarbon droplets coalesce in the upper region 72 of the disengagement zone 70 and exit the column through an outlet 74 as a single hydrocarbon phase, which is free or substantially free of water droplets but contains the desired dissolved water. The disengagement zone 70 is thus of sufficient height to allow the separation of entrained water and hydrocarbon to occur. Alternatively, a separate chamber is used for separating the entrained water droplets from the hydrocarbon stream.

Optionally, a portion of the resulting wet hydrocarbon stream may be recycled back to the bottom of the column via a recycle line 80 for another pass through the column (see FIG. 1). The pump 54 can be used to control the proportion returning to the column. Recycling the hydrocarbon stream in this way ensures that the wet hydrocarbon stream in the column is saturated with water, and tends to ensure that a more stable water content value is achieved. The portion which is recycled can vary, dependent on the flow rate of the hydrocarbon and the solubility of water in the hydrocarbon. At relatively low flow rates, particularly where the desired water concentration is less than the maximum achievable saturation limit, a single pass has been found to be adequate. At higher flow rates, 50% or more of the hydrocarbon stream may be recycled through the column. A non-return valve 82 in the return flow line 80 ensures that the fluids maintain the direction of flow as shown in FIG. 1.

The exiting wet hydrocarbon blend may be mixed with additional dry blend, to achieve a desired dissolved water content, although other methods of combining the two streams are also contemplated. FIG. 1 shows a static mixer 90 which combines wet and dry streams. For example, the water content may be reduced to 50% or 20% of the saturation limit by appropriate mixing of wet and dry blend streams. Specifically, a portion of the dry blend from the inlet line is fed via a direct line 92 to the mixer where it is mixed with the wet blend from the column. A valve 94 adjusts the portion of the dry blend which passes directly to the static mixer. The dry blend passing to the static mixer is preferably of the same hydrocarbon composition as that passing through the humidification column 10, although the dry blend can have a different hydrocarbon composition. If a fully water-saturated hydrocarbon stream is required, the step of mixing with a portion of the dry blend may, of course, be eliminated. In one embodiment, the humidified hydrocarbon stream includes about 200 ppm water. By combining this humidified hydrocarbon stream with a second portion of a hydrocarbon stream, a humidified hydrocarbon stream having a moisture content of from about 10 to about 150 ppm is obtained.

The mixed stream (the "humidified blend"), having a lower water content than the wet blend from the column, exits the mixer via an outlet line 96 which transports the humidified blend to a site 98 at which it is to be utilized, such as a polymerization reactor. Such reactors are disclosed, for example, in U.S. Pat. No. 4,472,559.

A moisture probe 100, fluidly coupled with the outlet line 96, detects the moisture content of the humidified blend and signals a moisture analyzer 102. The moisture analyzer provides an indication of the moisture level of the humidified blend. An operator may manually adjust the control valve 94 to set the ratio of dry to wet fraction or the control valve 94 may be adjusted automatically using a process loop controller 106, integral with or separate from the moisture analyzer 102, whose process variable input is the moisture level and whose output drives the control valve position. In this way, a desired output moisture level may be maintained.

The moisture probe 100 may be positioned directly in the outlet line 96 from the static mixer or, as shown in FIG. 1, may be positioned in a separate sampling chamber 110, into which a portion of the humidified blend is directed periodically for evaluation. In the embodiment of FIG. 1, a three way valve 112 in the outlet line is operated periodically to pass a sample of the humidified blend into the sampling chamber 110 through a sampling line 114. Optionally, a heater 118 in the sampling line heats the sample to a sufficient temperature to lower the relative humidity of the analyzed blend and thereby maintain the integrity of the probe 100. Water, which falls out of the humidified blend in the chamber, is carried out of the bottom of the chamber via a drain line 120 by periodically opening a drain valve 122.

The sampled humidified blend may be returned to the outlet line 96 or passed out of the sampling chamber 110 to a waste line 120 via valve 122. Alternatively, the sample may be returned to the column and mixed with the incoming dry blend.

After a sampling operation is complete, the sampling chamber 110 may be flushed with a dry fluid such as a dry hexane to remove traces of moisture from the chamber. For this purpose a three way valve 136 in the sampling line 114 is operated with the waste valve 122 open to carry the dry hexane purge through the sampling line and through the chamber 110, carrying any remaining wet hydrocarbon out of the chamber through the waste line 130. When another moisture determination is to be made, the hexane is flushed from the chamber by passing a portion of the wet blend through the chamber until a stable moisture content reading is obtained.

The system shown is set up for the periodic sampling of wet blend and for the subsequent draining and flushing of the moisture probe in an effort to maintain probe integrity, accuracy and longevity during process monitoring. The composition and construction of the moisture probe make it typically sensitive to high moisture levels and to process streams with high saturation levels. Using the probe for intermittent monitoring and by flushing the probe with dry solvent, maintains a long probe life and helps maintain the probe within its current calibration.

The system may include additional valves and regulators for regulating flow through the system, such as a pressure regulating valve 140 in the outlet line, which maintains the humidified blend and column at a positive pressure. This may be associated with a pressure transducer 142 for detecting the pressure in the outlet line. Other pressure transducers may be provided, for example, at 144, 146, 148, and 150. Other valves may be provided, such as a wet blend sampling valve 152, which allows a sample of the wet blend to be withdrawn from chamber 110 through a line 156 for analysis. A valve 158 may also be provided for closing off a line 160 between the chamber 70 and the liquid level gauge 32. A supplementary pressure relief valve 162 may be provided in a portion 164 of the inlet line, which carries both dry blend and recycled wet blend to the chamber. A valve 170 for closing off the line between the humidification system and the polymerization reactor may also be provided.

For a column of the dimensions described, flow rates of the humidified blend of about 20–50 liters per hour, or more are readily achieved. For larger columns, greater flow rates may be achieved.

When the water level in the column drops below a selected minimum level, typically just above the top of the dispersion material, the valve 34 is opened again to allow more water into the column. During the water addition, valve 60 may be closed. In this way, the system can be run relatively continuously for long periods of time.

The humidified hydrocarbon stream may be used as a process stream in a polymerization reaction which relies on the presence of small amounts of dissolved water to activate a catalyst for the polymerization reaction, such as the production of high cis-content polybutadiene with Ziegler Natta-type catalysts, such as those incorporating aluminum alkyls, alkyl chlorides, or aluminum alkoxides with a transition element, such as cobalt or nickel. Alternatively, or additionally the humidified hydrocarbon stream may be used for the in situ generation of catalyst systems, for example, the preparation of alkyl aluminoxanes, such as methyl aluminoxanes. This avoids the need to prepare the catalyst system in advance and store it in a toluene or similar hydrocarbon carrier liquid.

Without intending to limit the scope of the invention, the following example demonstrates the effectiveness of the humidification system.

EXAMPLE

A one meter tall column having three layers of porcelain beads (a lower layer 40 of a bead diameter of about 0.3 cm, an intermediate layer 42 of a diameter of about 0.6 cm and upper layer 44, of a diameter of about 1.3 cm occupying the lower 40 cm of the column) was filled about 50% with water. The pressure in the inlet line 50 was maintained at 10.5 kg/cm$^2$. A dry, 15% mixture of butadiene in hexane was fed to the column. The control valve 94 was opened at about 50% to mix about 50% dry blend with the wet blend exiting from the column. A flow rate of 22–45 liters per hour of a humidified blend containing a well-controlled 100 ppm moisture at an outlet pressure of 10 kg/cm$^2$ was achieved.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of humidifying a hydrocarbon stream comprising:
    passing the hydrocarbon stream through a bed comprising a packing material and water, thereby forming a humidified hydrocarbon stream.
2. The method of claim 1, wherein the packing material is in the form of particles.
3. The method of claim 1, wherein the hydrocarbon stream is passed upwardly through the bed.
4. The method of claim 3, wherein the packing material comprises particles, the particles having a smaller average diameter adjacent a bottom of the bed than adjacent a top of the bed.
5. The method of claim 4, wherein the particles in the bottom layer have an average diameter of approximately 0.2 to 0.5 centimeters and the particles in the top layer have an average diameter of approximately 1 to 1.5 centimeters.
6. The method of claim 1, wherein the packing material comprises porcelain.
7. The method of claim 1, wherein the hydrocarbon stream includes at least one hydrocarbon from monounsaturated alkanes and conjugated dienes.
8. The method of claim 7, wherein the hydrocarbon includes butadiene.
9. The method of claim 7, wherein the hydrocarbon stream further includes a solvent in which the hydrocarbon is soluble.
10. The method of claim 9, wherein the hydrocarbon comprises butadiene and the solvent comprises hexane.
11. The method of claim 1, further including, after the step of passing the hydrocarbon stream through the bed:
    allowing liquid water to fall out of the humidified hydrocarbon stream in a head space above the bed so that the humidified hydrocarbon stream is substantially free of undissolved water.

12. The method of claim 1, further including:
    combining the humidified hydrocarbon stream with a second portion of a hydrocarbon stream to achieve a desired moisture content.

13. The method of claim 12, wherein the humidified hydrocarbon stream includes about 200 ppm water and the step combining the humidified hydrocarbon stream with a second portion of a hydrocarbon stream results in a humidified hydrocarbon stream having a moisture content of from about 10 to about 150 ppm.

14. The method of claim 2, wherein said particles are spherical.

15. The method of claim 1, further including;
    recycling at least a portion of the humidified stream through the bed.

16. The method of claim 1, wherein the hydrocarbon stream is a liquid.

* * * * *